(12) United States Patent
Flachsmann

(10) Patent No.: US 11,359,161 B2
(45) Date of Patent: Jun. 14, 2022

(54) THIOETHER PRECURSORS FOR FRAGRANT KETONES AND ALDEHYDES

(71) Applicant: GIVAUDAN SA, Vernier (CH)

(72) Inventor: Felix Flachsmann, Duebendorf (CH)

(73) Assignee: GIVAUDAN SA, Vernier (CH)

( * ) Notice: Subject to any disclaimer, the term of this patent is extended or adjusted under 35 U.S.C. 154(b) by 44 days.

(21) Appl. No.: 16/966,720

(22) PCT Filed: Feb. 21, 2019

(86) PCT No.: PCT/EP2019/054296
§ 371 (c)(1),
(2) Date: Jul. 31, 2020

(87) PCT Pub. No.: WO2019/166315
PCT Pub. Date: Sep. 6, 2019

(65) Prior Publication Data
US 2021/0032562 A1    Feb. 4, 2021

(30) Foreign Application Priority Data
Mar. 2, 2018 (EP) ..................... 18159756

(51) Int. Cl.
C11D 3/50 (2006.01)
C11B 9/00 (2006.01)
(Continued)

(52) U.S. Cl.
CPC ............ C11B 9/0011 (2013.01); C07C 45/65 (2013.01); C07C 319/06 (2013.01); C11B 9/003 (2013.01);
(Continued)

(58) Field of Classification Search
CPC .................... C11D 3/50; C11D 3/507
See application file for complete search history.

(56) References Cited

U.S. PATENT DOCUMENTS 4,560,799 A    12/1985  Spivack et al.
2006/0040848 A1*  2/2006  Fehr .................... A61K 8/37
                                              512/8
(Continued)

FOREIGN PATENT DOCUMENTS

CN    1709867 A    12/2005
CN    103073454 A   5/2013
(Continued)

OTHER PUBLICATIONS

International Search Report and Written Opinion of the International Searching Authority for corresponding application PCT/EP2019/054296 dated May 22, 2019.
(Continued)

Primary Examiner — John R Hardee
(74) Attorney, Agent, or Firm — Norris McLaughlin PA

(57) ABSTRACT

Disclosed is a use of a compound of formula (I), a composition of matter comprising a compound of formula (I) and a consumer product comprising a compound of formula (I).

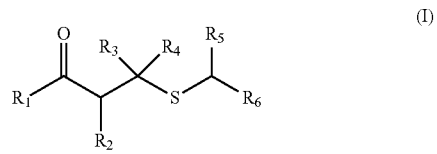

23 Claims, 2 Drawing Sheets

Figure 1:
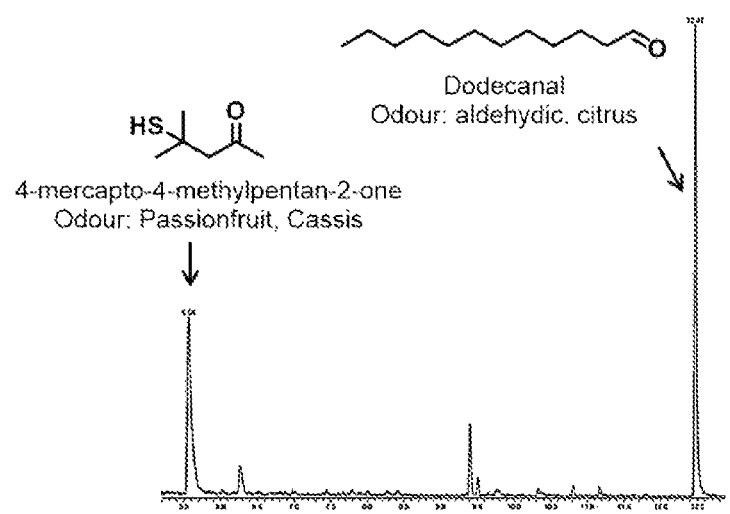

(51) Int. Cl.
C07C 45/65 (2006.01)
C07C 319/06 (2006.01)
(52) U.S. Cl.
CPC .......... *C11B 9/0034* (2013.01); *C11B 9/0061* (2013.01); *C11D 3/50* (2013.01); *C07C 2601/08* (2017.05); *C07C 2601/14* (2017.05); *C07C 2601/16* (2017.05)

(56) References Cited

U.S. PATENT DOCUMENTS

| | | | | |
|---|---|---|---|---|
| 2013/0324450 | A1* | 12/2013 | Reichlin | C11D 3/349 510/103 |
| 2014/0323383 | A1* | 10/2014 | Trujillo | C11D 17/043 510/439 |
| 2015/0045274 | A1* | 2/2015 | Fankhauser | C11B 9/0034 510/105 |

FOREIGN PATENT DOCUMENTS

| | | |
|---|---|---|
| EP | 0936211 A2 | 8/1999 |
| GB | 1457089 | 12/1976 |
| WO | 03049666 A2 | 6/2003 |
| WO | 2004105713 A1 | 12/2004 |
| WO | 2007143873 A1 | 12/2007 |
| WO | 2008093272 A2 | 8/2008 |
| WO | 2008142591 A2 | 11/2008 |
| WO | 2009118219 A1 | 10/2009 |
| WO | 2010020954 A1 | 2/2010 |
| WO | 2010029462 A1 | 3/2010 |
| WO | 2010066486 A2 | 6/2010 |
| WO | 2010094256 A1 | 8/2010 |
| WO | 2010094356 A1 | 8/2010 |
| WO | 2010105873 A2 | 9/2010 |
| WO | 2010105874 A1 | 9/2010 |
| WO | 2011101179 A1 | 8/2011 |
| WO | 2011101180 A1 | 8/2011 |
| WO | 2012126675 A1 | 2/2012 |
| WO | 2012085287 A1 | 6/2012 |
| WO | 2012113746 A1 | 8/2012 |
| WO | 2012130739 A1 | 10/2012 |
| WO | 2012139912 A1 | 10/2012 |
| WO | 2013139766 A2 | 9/2013 |
| WO | 2014176392 A1 | 10/2014 |
| WO | 2014180782 A1 | 11/2014 |
| WO | 2014180791 A1 | 11/2014 |
| WO | 2015032885 A1 | 3/2015 |
| WO | 2015093572 A1 | 6/2015 |
| WO | 2016074695 A1 | 5/2016 |
| WO | 2016074699 A1 | 5/2016 |
| WO | 2016091894 A1 | 6/2016 |
| WO | 2016091899 A1 | 6/2016 |
| WO | 2016096539 A1 | 6/2016 |
| WO | 2016096540 A1 | 6/2016 |
| WO | 2016116420 A1 | 7/2016 |
| WO | 2016135193 A1 | 9/2016 |
| WO | 2018096176 A1 | 5/2018 |

OTHER PUBLICATIONS

EP Search Report for corresponding application EP 18159756.8 dated Sep. 11, 2018.
U. Maddalena, et al: "Thioether Profragrances: Parameters Influencing the Performance of Precursor Based Fragrance Delivery in Functional Perfumery", Chemistry & Biodiversity, vol. 11, No. 11, 2014, pp. 1700-1733, XP055502263.
S. Ohashi et al.: "Asymmetric addition catalyzed by optically active polymers. III.", Die Makromolekulare Chemie, vol. 160, No. 1, 1972, pp. 69-81, XP055502387.
Database Caplus [Online] Chemical Abstracts Service, Columbus, Ohio, US; 2013, Ciganek, Engelbert: "Electrophilic amination of carbanions, enolates, and their surrogates", XP002784204.
J.R. Catch, et al.: "320.Syntheses of some amino-acids, including methionine", Journal of the Chemical Society (Resumed), 1947, pp. 1609-1613, XP055085742.
A. Peng, et al.:"Conjugate addition of unactivated thiols to alpha, beta-unsaturated ketones catalyzed by a bifunctional rhenium(V)-oxo complex", Tetrahedron Letters, vol. 53, No. 22, 2012, pp. 2712-2714, XP028419281.
Sirotanovic, K.D. et al.: "Addition of Mercaptans to Unsaturated Aldehydes.III. Preparation of Bisurethanes and Bisamides of [beta]-alkylmercapto-aldehydes and [beta]-arylmercapto-aldehydes", Glasnik Hemijskog Drustva Beograd, vol. 31, No. 7-8, 1966, pp. 49 (339)-58 (349), XP009507636.
Matsuo, J.-I. et al.: "Bronsted Acid Catalyzed Asymmetric Reduction of Ketones and Acyl Silanes Using Chiral anti-Pentane-2,4-diol", Organic Letters, vol. 12, No. 10, 2010, pp. 2294-2297, XP055502012.
Matsuo, J.-I. et al.: "Asymmetric reduction of aliphatic ketones and acyl silanes using chiral anti-pentane-2,4-diol and a catalytic amount of 2,4-dinitrobenzenesulfonic acid", Tetrahedron, vol. 66, No. 32, 2010, pp. 6062-6069, XP027142126.
Zdansky, G. et al.: "5-(Benzylthioalkyl)- and 5-(benzylselenoalkyl)-substituted hydantoins. Some notes on the hydantoin synthesis for the preparation of selenoamino acids", Arkiv Foer Kemi, vol. 29, No. 4, 1968, pp. 47-56, XP009507637.
Wabnitz, T.C. et al.: "A General, Bronsted Acid-Catalyzed Hetero-Michael Addition of Nitrogen, Oxygen, and Sulfur Nucleophiles", Organic Letters, vol. 5, No. 12, 2003, pp. 2141-2144, XP055501960.
Emori, E. et al.: "A Catalytic Michael Addition of Thiols to [alpha],[beta]-Unsaturated Carbonyl Compounds: Asymmetric Michael Additions and Asymmetric Protonations", Journal of the American Chemical Society, vol. 120, No. 16, 1998, pp. 4043-4044, XP055501712.
Garg, S.K. et al.: "Copper(II) tetrafluoroborate as a novel and highly efficient catalyst for Michaeladdition of mercaptans to alpha,beta-unsaturated carbonyl compounds", Tetrahedron Letters, vol. 46, No. 10, 2005, pp. 1721-1724, XP027862306.
Ramachary, D.B. et al.: "Direct organocatalytic hydroalkoxylation of alpha, beta-unsaturated ketones", Tetrahedron Letters, vol. 47, No. 44, 2006, pp. 7689-7693, XP025003078.
International Search Report for related application PCT/EP2019/054294 dated Apr. 12, 2019.
GB Search Report for corresponding application GB1803410.8 dated Oct. 26, 2018.
Tian, et al., "Diastereodivergent Asymmetric Sulfa-Michael Additions of alpha-Branched Enones using a Single Chiral Organic Catalyst", Journal of the American Chemical Society, vol. 133, 2011, pp. 17934-17941.
Lanari, et al., "JandaJel as a polymeric support to improve the catalytic efficiency of immobilized-1,5,7-triazabicyclo[4.4.0]dec-5-ene (TBD) under solvent-free conditions", Green Chemistry, vol. 13, 2011, pp. 3181-3186.
Hache, et al., "Free-Radical Addition to Olefins of an H2S Equivalent: Triphenylsilanethiol", Tetrahedron Letters, vol. 35, No. 12, pp. 1837-1840, 1994, Great Britain.
Herrmann, et al., "Controlled Release of Volatile Under Mild Reaction Conditions: From Naturev to Everyday Products", Angew. Chem. Ind. Ed., 2007, 46, pp. 5836-5863.
Bonollo, et al., "Sc(III)-catalyzed Enantioselective Addition of Thiols to alpha,beta-Unsaturated Ketones in Neutral Water", Organic Letters, vol. 13, 2011, pp. 2150-2152.

* cited by examiner

THIOETHER PRECURSORS FOR FRAGRANT KETONES AND ALDEHYDES

This is an application filed under 35 USC 371 based on PCT/EP2019/054296, filed 21 Feb. 2019, which in turn is based on EP 18159756.8 filed 2 Mar. 2018. The present application claims the full priority benefit of these prior applications and herein incorporates by reference the full disclosures of these prior applications.

The present invention relates to a use of a compound of formula (I), to a composition of matter comprising a compound of formula (I) and to a consumer product comprising a compound of formula (I) according to the independent claims.

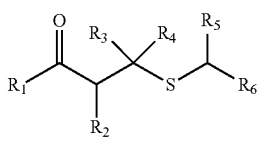
(I)

Fruity, exotic, blackcurrant or passionfruit notes are popular in perfumery and constitute attractive alternatives to hesperidic-citrus, lavender or aldehydic scents. They are not only used in fine fragrances but also in other applications, such as cosmetic, laundry and cleaning products. Representative examples of this kind of fragrance ingredient include Corps Cassis (4-(methylthio)-4-methyl-2-pentanone), Oxane ((2R, 4S)-2-methyl-4-propyl-1,3-oxathiane) and Cassyrane (5-tert-butyl-2-methyl-5-propyl-2H-furan). Generally, blackcurrant notes are top notes that consist of small molecules with a relatively low molecular weight that evaporate quickly. Since they are perceived immediately after application of a perfume, top notes are important for the initial impression thereof.

However, top notes also have a relatively low persistence and are often perceived only over a short period of time. High volatility and poor substantivity can be a problem when a prolonged effect of a fragrance is required, both in fine and functional perfumery. By way of example, laundry applications require continuous effectiveness of a perfume over a certain period of time after washing and drying of the textiles. Also in household care applications a prolonged effectiveness of perfumes can be required.

It is therefore a problem underlying the present invention to overcome these drawbacks in the prior art. In particular, it is a problem underlying the present invention to provide blackcurrant or passionfruit notes for fragrances that have an increased persistence and can be perceived over a prolonged period of time. Additionally, these notes should be versatile in application and inexpensive in production.

These problems are solved by use of a compound of formula (I) according to claim 1. Specifically, the compound of formula (I) is used as a precursor for generating a compound of formula (II) and/or a compound of formula (III).

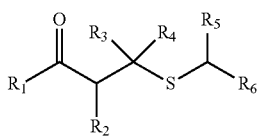
(I)

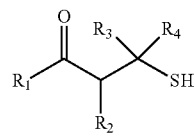
(II)

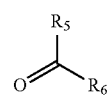
(III)

In the above formulas (I), (II) and (III), $R_1$ is H or $C_{1-5}$-alkyl; $R_2$ is H or $C_{1-5}$-alkyl; $R_3$ is H or $C_{1-5}$-alkyl; and $R_4$ is $C_{1-6}$-alkyl; or $R_1$ and $R_4$ together with the carbon atoms to which they and $R_2$ are attached form a 5, 6 or 7 membered ring, preferably a hydrocarbon ring; $R_2$ is H or $C_{1-4}$-alkyl; and $R_3$ is H or $C_{1-4}$-alkyl; and wherein $R_5$ is H or a residue comprising 1 to 20 carbon atoms; and $R_6$ is a residue comprising 3 to 20 carbon atoms.

β-Thiocarbonyl compounds are known in the prior art as precursors for the generation of fragrance molecules, as for instance described in WO 2003/049666 A2. However, only cleavage of the bond between the sulfur atom and the carbon atom in β-position to the carbonyl group (herein referred to as "γ-cleavage") has been reported in the literature. This reaction pathway generally leads to the liberation of a corresponding α,β-unsaturated carbonyl compound (not shown here).

It has now been found that β-thiocarbonyl compounds according to the present invention undergo cleavage of the bond between the sulfur atom and the carbon atom in δ-position to the carbonyl group (herein referred to as "δ-cleavage").

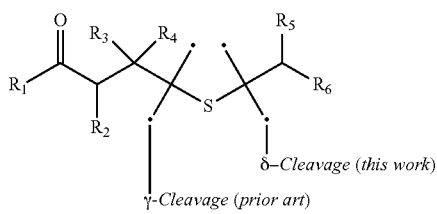

This newly discovered reactivity allows for use of a compound of formula (I) as a precursor for generating a compound of formula (II), namely a β-thiocarbonyl compound. This is particularly useful for release of fragrance notes with an exotic, fruity, blackcurrant or passionfruit character, as discussed in further detail herein below. Depending on the structure of residues $R_1$ to $R_4$, the odor properties of the compound of formula (II) can be adapted according to a specific application.

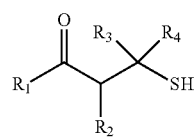
(II)

Another aspect of the present invention relates to the discovery that with compounds of formula (I) also carbonyl compounds of formula (III) are generated. This allows for use of a compound of formula (I) as a precursor for generating a compound of formula (III), in particular an aldehyde or a ketone. Since many perfume ingredients comprising a carbonyl group are known in the prior art, depending on the structure of residues $R_5$ and $R_6$, the odor properties of the compound of formula (III) can be adapted according to a specific application.

(III)

The compound of formula (I) can therefore also be used as a precursor for a carbonyl compound of formula (III). In a particularly useful embodiment, the compound of formula (I) can also be used as a precursor for compounds of formulas (II) and (III). In the present context, such a precursor is referred to as a "bifragrant precursor".

The structure of residues $R_1$ to $R_6$ plays an important role with respect to the kinetics for the release of the compounds of formula (II) and/or formula (III). In the context of the present invention, the compound of formula (I) may in addition to δ-cleavage also undergo γ-cleavage. By careful choice of the residues $R_1$ to $R_6$, it is possible to tune the fragrance release properties of a compound of formula (I).

The person skilled in the art is familiar with the conditions under which fragrance precursors are generally used. More specifically, use of a compound of formula (I) according to the present invention commonly takes place under ambient air at a temperature of −20° C. to 100° C., preferably −10° C. to 60° C., even more preferably 0° C. to 40° C., in particular at room temperature.

Another aspect of the present invention relates to a method for generating a compound of formula (II) and/or a compound of formula (III) by decomposition of a compound of formula (I). The compounds of formula (I), (II) and (III) have the structures as defined herein above.

A further aspect of the present invention refers to a composition of matter comprising a compound of formula (I) and a compound of formula (A).

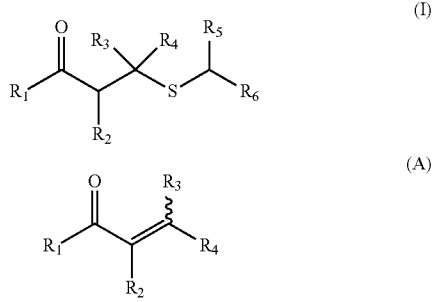

In the above formulas (I) and (A), $R_1$ is H or $C_{1-5}$-alkyl; $R_2$ is H or $C_{1-5}$-alkyl; $R_3$ is H or $C_{1-5}$-alkyl; and $R_4$ is $C_{1-6}$-alkyl; or $R_1$ and $R_4$ together with the carbon atoms to which they and $R_2$ are attached form a 5, 6 or 7 membered ring, preferably a hydrocarbon ring; $R_2$ is H or $C_{1-4}$-alkyl; and $R_3$ is H or $C_{1-4}$-alkyl; and wherein $R_5$ is H or a residue comprising 1 to 20 carbon atoms; and $R_6$ is a residue comprising 3 to 20 carbon atoms.

In the context of the present application, a curly bond (cf. $R_3$ in formula (A)) means that the configuration at a given center is undefined. The double bond in formula (A) may thus be either (E) or (Z).

In a composition of matter as specified herein above, $R_1$, $R_2$, $R_3$, $R_4$, $R_5$ and $R_6$ can be the same for both of the compound of formula (I) and the compound of formula (A), or they can be different. Preferably, they are the same.

In compositions of matter as specified herein above, it has been found that the occurrence of thiol off-odors is suppressed when a compound of formula (A) is present. Consequently, beneficial olfactory properties can be achieved.

In case the proportion of the compound of formula (A) is increased over a certain level, its odor can become prevalent and disturb the overall olfactory appearance of the composition. Thus, the amount of the compound of formula (A) in relation to the total amount of the compound of formula (I) and the compound of formula (A) is 0.1-3.0 wt.-%, preferably 0.3-1.2 wt.-%, even more preferably 0.6-1.0 wt.-%.

In yet another aspect, the present invention refers to a consumer product comprising a compound of formula (I).

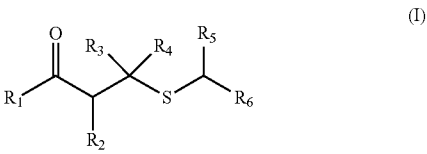

(I)

In the above formula (I), $R_1$ is H or $C_{1-4}$-alkyl; $R_2$ is H or $C_{1-4}$-alkyl; $R_3$ is H or $C_{1-4}$-alkyl; and $R_4$ is $C_{1-4}$-alkyl; or $R_1$ and $R_4$ together with the carbon atoms to which they and $R_2$ are attached form a 5, 6 or 7 membered ring, preferably a hydrocarbon ring; $R_2$ is H or $C_{1-4}$-alkyl; and $R_3$ is H or $C_{1-4}$-alkyl.

Furthermore, $R_5$ is H or a residue comprising 1 to 20 carbon atoms; and $R_6$ is a residue comprising 6 to 20 carbon atoms.

The total combined number of carbon atoms of $R_1$, $R_2$, $R_3$ and $R_4$ is 1 to 4, preferably 1 to 3.

In a use of a compound of formula (I) and/or in a composition of matter comprising a compound of formula (I) and a compound of formula (A) as specified herein above, the total combined number of carbon atoms of $R_1$, $R_2$, $R_3$ and $R_4$ can be 1 to 6, preferably 1 to 5, more preferably 1 to 4, even more preferably 1 to 3, irrespective of the nature of $R_5$ and $R_6$.

This selection of residues $R_1$, $R_2$, $R_3$ and $R_4$ has the advantage that compounds of formula (II) generated, due to their low molecular weight, generally have a high vapor pressure which leads to an increased perception of their odor. This is particularly useful when strong fruity, blackcurrant notes are to be generated.

In a use of a compound of formula (I), in a composition of matter comprising a compound of formula (I) and a compound of formula (A), and/or in a consumer product comprising a compound of formula (I) as described herein above, $R_1$, $R_2$, $R_3$ and $R_4$ can have the following structures, either alone or in combination:

$R_1$ can be selected from the group consisting of methyl, ethyl, n-propyl, iso-propyl, n-butyl, sec-butyl and tert-butyl;

$R_2$ can be selected from the group consisting of methyl, ethyl, n-propyl, iso-propyl, n-butyl, sec-butyl and tert-butyl;

$R_3$ can be selected from the group consisting of methyl, ethyl, n-propyl, iso-propyl, n-butyl, sec-butyl and tert-butyl;

$R_4$ can be selected from the group consisting of methyl, ethyl, n-propyl, iso-propyl, n-butyl, sec-butyl and tert-butyl.

In a use of a compound of formula (I), in a composition of matter comprising a compound of formula (I) and a compound of formula (A), and/or in a consumer product comprising a compound of formula (I) as described herein above, the following combinations of $R_1$ and $R_4$ are particularly preferred:

$R_1$ is H and $R_4$ is H;
$R_1$ is H and $R_4$ is methyl;
$R_1$ is methyl and $R_4$ is H;
$R_1$ is methyl and $R_4$ is methyl.

In a use of a compound of formula (I), in a composition of matter comprising a compound of formula (I) and a compound of formula (A), and/or in a consumer product comprising a compound of formula (I) as described herein above, the following combination of $R_1$, $R_2$, $R_3$ and $R_4$ is particularly preferred:

$R_1$ is H; $R_2$ is H; $R_3$ is H; and $R_4$ is methyl
$R_1$ is H; $R_2$ is H; $R_3$ is methyl; and $R_4$ is methyl;
$R_1$ is methyl; $R_2$ is H; $R_3$ is H; and $R_4$ is methyl;
$R_1$ is methyl; $R_2$ is H; $R_3$ is methyl; and $R_4$ is methyl.

These compounds show a preferred release profile for ketones and aldehydes, which have proven to be useful in perfumery due their beneficial organoleptic properties. The fourth combination of residues leads to the generation of the fruity, exotic, blackcurrant and passionfruit fragrance note 4-mercapto-4-methyl-2-pentanone through δ-cleavage.

In a use of a compound of formula (I), in a composition of matter comprising a compound of formula (I) and a compound of formula (A), and/or in a consumer product comprising a compound of formula (I) as specified herein above, $R_5$ and $R_6$ can have the following structural features, either alone or in combination:

$R_5$ can be a residue comprising 4 to 18 carbon atoms, preferably 6 to 16 carbon atoms;
$R_5$ can be an alkyl, alkenyl or aromatic residue;
$R_6$ can be a residue comprising 7 to 16 carbon atoms, preferably 8 to 14 carbon atoms, even more preferably 9 to 13 carbon atoms;
$R_6$ can be an alkyl, alkenyl or aromatic residue.

In $R_5$ and/or $R_6$, the alkyl or alkenyl residues can be linear, cyclic or branched.

$R_5$ and/or $R_6$ can be hydrocarbon residues. However, they can also have one or more heteroatoms, in particular one, two or three oxygen atoms. The oxygen atoms can be part of ether and ester groups.

In a use of a compound of formula (I), in a composition of matter comprising a compound of formula (I) and a compound of formula (A), and/or in a consumer product comprising a compound of formula (I) according to the present invention, the compound of formula (I) can be selected from the group consisting of 3-(octylthio)butanal, 4-methyl-4-(octylthio)pentan-2-one, 3-(decylthio)butanal, 4-(decylthio)-4-methylpentan-2-one, 4-(dodecylthio)pentan-2-one, 4-(dodecylthio)-4-methylpentan-2-one, 4-(dodecylthio)-3-methylpentan-2-one, 3-(dodecylthio)-3-methylbutanal, 3-(dodecylthio)butanal, 3-(dodecylthio)-3-methylcyclohexan-1-one, 3-(dodecylthio)-3-methylcyclopentan-1-one, 3-(tetradecylthio)butanal, 4-methyl-4-(tetradecylthio)pentan-2-one, 4-methyl-4-((6-methyloctyl)thio) pentan-2-one, 3-((3-(4-isobutyl-2-methylphenyl)propyl)thio)butanal and 4-((3-(4-isobutyl-2-methylphenyl)propyl)thio)-4-methylpentan-2-one.

These compounds can be prepared in an efficient and inexpensive manner by 1,4-addition of a linear alkylthiol to an α,β-unsaturated carbonyl compound, as will be discussed in more detail herein below. When γ-cleavage occurs as a side reaction, the thiols generated have a low vapor pressure and are therefore not perceived as a disturbing off-odor. Furthermore, the aldehydes of formula (III) that can be concomitantly generated have by themselves an odor profile that is useful in perfumery. By means of simultaneous release, a particular impression of freshness can be achieved.

The present invention also refers to a fragrance oil or a fragrance composition comprising a composition of matter comprising a compound of formula (I) and a compound of formula (A) as herein defined.

In the context of the present invention, the term "fragrance oil" is to be understood as a mixture of fragrance ingredients.

In the context of the present invention, a "fragrance composition" is to be understood as a fragrance ingredient or a fragrance oil that has been mixed with a base material.

The base material can comprise a diluent, such as diethyl phthalate (DEP), dipropylene glycol (DPG), isopropyl myristate (IPM), triethyl citrate (TEC) or an alcohol, for instance ethanol.

The present invention also relates to a consumer product comprising a composition of matter comprising a compound of formula (I) and a compound of formula (A) as specified herein above. The consumer product can be a personal care product, a laundry care product or a household care product. Examples of such products include cosmetics, shampoos, shower gels, deodorants, antiperspirants, laundry detergents, rinse conditioners, fabric softeners, detergents for dishwashers, surface cleaners, in particular for hard and soft surfaces and air care products.

Disclosed is also a method for producing a fragrance ingredient comprising a compound of formula (I) by reaction of a compound of formula (A) with a compound of formula (B).

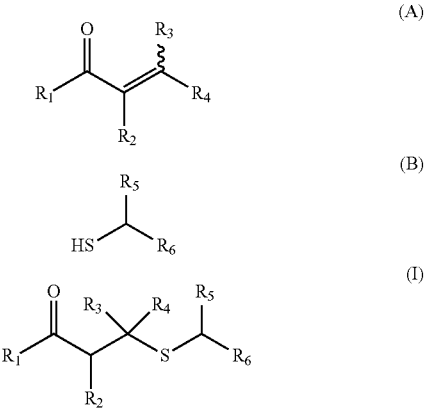

The above-mentioned method can comprise the step of forming a mixture of the compound of formula (A) with the compound of formula (B) in a solvent, wherein the solvent is preferably an alcohol or an ether, in particular selected from the group consisting of methanol, ethanol, n-propanol, iso-propanol, n-butanol, sec-butanol, tert-butanol, diethyl ether, diisopropyl ether, di-n-butyl ether, methyl tert-butyl ether, tetrahydrofuran and 2-methyl tetrahydrofuran.

On the other hand, reaction of a compound of formula (A) with a compound of formula (B) can also be conducted in the substantial absence of a solvent.

The reaction of a compound of formula (A) with a compound of formula (B) can be conducted in the presence of a base, preferably selected from the group consisting of DBU (1,8-diazabicyclo(5.4.0)undec-7-ene), trimethylamine, trimethylamine, N,N-diisopropylethylamine and urotropine.

When $R_1$ is H, it is preferred to conduct the reaction in the substantial absence of any base and in a protic solvent, preferably an alcohol, in particular selected from the group consisting of methanol, ethanol, n-propanol, iso-propanol, n-butanol, sec-butanol, tert-butanol.

In the reaction of the compound of formula (A) with the compound of formula (B), the molar ratio of the compound of formula (A) and the compound of formula (B) can be between 5:1 and 1:1, preferably between 2:1 and 1.05:1. This has the advantage that removal of a large excess of the compound of formula (B) is avoided.

The above-mentioned method can further comprise the step of purifying the compound of formula (I) obtained, preferably by distillation, in particular wiped film distillation, or chromatography.

Further advantages and particular features of the present invention become apparent form the following discussion of several examples and from the figures.

Example 1: 4-(Dodecylthio)-4-methylpentan-2-one

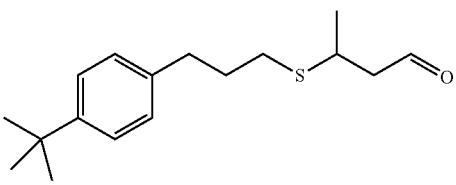

1-Dodecanethiol (30.0 g, 148 mmol, 1 equiv.), 4-methyl-pent-3-en-2-one (29.1 g, 2 equiv.) and DBU (22.6 g, 1 equiv.) were dissolved in THF (200 mL) and the solution was stirred for 24 h at room temperature, after which it was diluted with hexane (200 mL) and poured on 2M aqueous HCl-solution (400 mL). The organic layer was separated, washed with water and brine (pH 6), dried over MgSO$_4$, filtered by suction and evaporated in a rotatory evaporator. The resulting liquid was further dried under high vacuum at 60° C./0.08 mbar to yield 4-(dodecylthio)-4-methylpentan-2-one as a clear, yellow liquid (44.5 g, 100%).

Odor (1% wt/vol in EtOH on blotter after 24 h): cassis, mango, passionfruit, juicy, lindenblossom $^1$H-NMR (CDCl$_3$, 400 MHz): 2.69 (s, 2H), 2.54 (t, J=7.3 Hz, 2H), 2.20 (s, 3H), 1.51-1.62 (m, 2H), 1.42 (s, 6H), 1.34-1.23 (m, 18H), 0.88 (t, J=6.6 Hz, 3H).

$^{13}$C-NMR (CDCl$_3$, 101 MHz): 206.9 (s), 54.7 (t), 43.3 (s), 32.3 (q), 31.9 (t), 29.6 (3 t), 29.5 (2 t), 29.4 (3 t), 29.3 (2 t), 28.5 (2 q), 28.1 (t), 22.7 (t), 14.1 (q).

MS (EI, 70 eV): 300 (2, M$^+$), 98 (15), 83 (34), 69 (16), 57 (15), 56 (15), 55 (41), 43 (100), 41 (36), 39 (16), 29 (23).

Example 2: 4-Methyl-4-((2-methylundecyl)thio)pentan-2-one

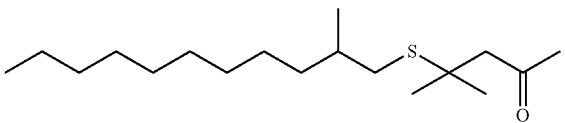 [SMILES: CCCCCCCCCC(C)CSC(C)(C)CC(C)=O]

The procedure described in Example 1 was repeated with 2-methylundecane-1-thiol (preparation see B. Hache, Y. Gareau, Tetrahedron Lett. 1994, 35(12), 1837), (8.0 g, 39.5 mmol, 1 equiv.), 4-methylpent-3-en-2-one (7.76 g, 2 equiv.) and DBU (6.0 g, 1 equiv.) in THF (80 mL). The crude product was purified by FC with hexane/MTBE 96:4 to yield 4-methyl-4-((2-methylundecyl)thio)pentan-2-one as a colorless liquid (5.95 g, 50%).

Odor (1% wt/vol in EtOH on blotter after 24 h): green, tomato leaves, cassis $^1$H-NMR (CDCl$_3$, 400 MHz): 2.69 (s, 2H), 2.53 (dd, J=11.4, 5.7 Hz, 1H), 2.38 (dd, J=11.2, 7.3 Hz, 1H), 2.20 (br s, 3H), 1.56-1.71 (m, 1H), 1.42 (br s, 6H), 1.24-1.30 (m, 16H), 0.98 (d, J=6.6 Hz, 3H), 0.89 (t, J=6.6 Hz, 3H).

$^{13}$C-NMR (CDCl$_3$, 101 MHz): 207.0 (s), 54.7 (t), 43.1 (s), 36.5 (t), 35.4 (t), 33.5 (d), 32.4 (q), 31.9 (t), 29.8 (t), 29.6 (t), 29.6 (t), 29.3 (t), 28.5 (2q), 27.0 (t), 22.7 (t), 19.7 (q), 14.1 (q).

MS (EI, 70 eV): 300 (2, M$^+$), 201(16), 99 (22), 83 (29), 69 (15), 57 (26), 56 (15), 55 (31), 43 (100), 41 (33), 29 (19).

Example 3: 3-((3-(4-(tert-Butyl)phenyl)propyl)thio)butanal

3a) Preparation of 3-(4-(tert-butyl)phenyl)propane-1-thiol

This thiol was prepared by tosylation of the corresponding alcohol, nucleophilic substitution with potassium thioacetate and reduction of the thioester to the free thiol as described in the following:

3-(4-(tert-Butyl)phenyl)propan-1-ol (32.7 g, 170 mmol, 1 equiv.) was dissolved in MTBE (100 mL) and tosyl chloride (33.5 g, 1 equiv.) was added. The solution was cooled to 5° C., then pyridine (29.0 g, 2.1 equiv.) was added dropwise over 15 min. The cooling bath was removed and the solution was heated to 60° C. for 6 h under stirring. The solution was diluted with water and extracted with MTBE. The combined organic layers were washed with 0.5 M HCl, then with water and brine and dried over MgSO$_4$. The solvents were removed by rotary evaporation, and the residue was dried at room temperature at 0.08 mbar. The tosylate, a slightly yellow, viscous oil, was dissolved in DMF (170 mL) and potassium thioacetate (39.2 g, 2.0 equiv.) was added and the resulting brown suspension was heated to 80° C. for 2 h, cooled to room temperature and left stirring for 16 h. The suspension was then diluted with MTBE/hexane 1:1 and washed with brine/water 1:1, then with brine. The organic layer was separated and dried over MgSO$_4$. After evaporation of the solvent, a dark red-brown oil was obtained (36 g) with intense sulfury smell. This product was dissolved in diethyl ether (200 mL) and added dropwise to a cooled (−10° C.) suspension of LiAlH$_4$ (5.46 g, 144 mmol) in diethyl ether (100 mL) during 20 min. The temperature rose to 5° C. The resulting suspension was further stirred for 2 h at 5° C., then cooled to −5° C. Saturated aqueous NH$_4$Cl solution (50 mL) was added dropwise, which caused a strong hydrogen evolution. Upon the addition of 2 M aqueous HCl solution (80 mL), a voluminous precipitate was formed. The slurry was diluted with MTBE and water and the aqueous layer was further extracted with MTBE. The combined organic layers were washed with brine and dried over MgSO$_4$. The crude light brown oil (25.3 g) with strong sulfury smell obtained after removal of the solvent was used directly for the preparation of the subsequent 1,4-addition reactions.

3b) Preparation of 3-((3-(4-(tert-butyl)phenyl)propyl)thio)butanal 3-(4-(tert-Butyl)phenyl)propane-1-thiol (2.14 g, 10.2 mmol, 1 equiv.) was dissolved in EtOH (5 mL) and the solution of (E)-but-2-enal (0.9 g, 1.2 equiv.) in EtOH (3 mL) was added dropwise. The resulting solution was stirred for 3 days at room temperature, then concentrated in a rotatory evaporator under reduced pressure and the residue was purified by FC using hexane/MTBE 9:1 to yield 3-((3-(4-(tert-butyl)phenyl) propyl)thio)butanal (2.15 g, 75%) as a colorless oil.

Odor (1% wt/vol in EtOH on blotter after 24 h): aldehydic, fruity, cassis $^1$H-NMR (CDC$_3$, 400 MHz): 9.79 (t, J=1.9 Hz, 1H), 7.33-7.39 (m, 2H), 7.14-7.19 (m, 2H), 3.31 (sxt, J=6.9 Hz, 1H), 2.57-2.77 (m, 6H), 1.95 (quin, J=7.5 Hz, 2H), 1.38 (d, J=6.8 Hz, 3H), 1.36 (s, 9H).

$^{13}$C-NMR (CDCl$_3$, 101 MHz): 201.0 (s), 149.2 (s), 138.7 (s), 128.5 (2d), 125.7 (2d), 50.9 (t), 34.8 (s), 34.7 (t), 34.5 (d), 31.9 (3q), 31.6 (t), 30.5 (t), 22.2 (q).

MS (EI, 70 eV): 278 (2, M$^+$), 208 (27), 193 (100), 159 (62), 131 (43), 117 (49), 115 (25), 91 (31), 57 (18), 41 (30), 39 (17).

Example 4: 4-((3-(4-(tert-butyl)phenyl)propyl)thio)-4-methylpentan-2-one

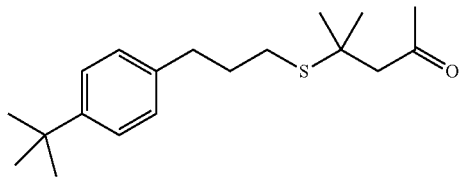 [SMILES: CC(=O)CC(C)(C)SCCCc1ccc(C(C)(C)C)cc1]

The procedure described in Example 1 was repeated with 3-(4-(tert-butyl)phenyl)propane-1-thiol (prepared in example 3a) (2.12 g, 10.2 mmol, 1 equiv.), 4-methylpent-3-en-2-one (1.0 g, 1 equiv.) and DBU (1.54 g, 1 equiv.) in ethanol (5 mL). The crude product was purified by FC with hexane/MTBE 19:1 to yield 4-((3-(4-(tert-butyl)phenyl)propyl)thio)-4-methylpentan-2-one as a colorless liquid (2.22 g, 71%).

Odor (1% wt/vol in EtOH on blotter after 24 h): fruity, cassis $^1$H-NMR (CDCl$_3$, 400 MHz): 7.31-7.37 (m, 2H), 7.13-7.19 (m, 2H), 2.69-2.76 (m, 4H), 2.60 (t, J=7.3 Hz, 2H), 2.20 (s, 3H), 1.92 (quin, J=7.3 Hz, 2H), 1.44 (s, 6H), 1.34 (s, 9H).

$^{13}$C-NMR (CDCl$_3$, 101 MHz): 207.3 (s), 149.1 (s), 138.8 (s), 128.5 (2d), 125.7 (2d), 55.1 (t), 43.9 (s), 35.0 (t), 34.8 (s), 32.8 (q), 31.8 (3q), 31.5 (t), 28.9 (2q), 28.0 (t).

MS (EI, 70 eV): 306 (3, M$^+$), 208 (30), 193 (100), 159 (81), 131 (42), 117 (68), 91 (39), 83 (32), 57 (42), 55 (34), 43 (75).

Example 5: 4-Methyl-4-(phenethylthio)pentan-2-one

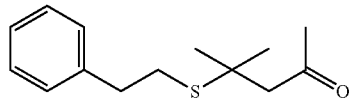 [SMILES: CC(=O)CC(C)(C)SCCc1ccccc1]

The procedure described in Example 1 was repeated with 2-phenylethane-1-thiol (5.0 g, 36.2 mmol, 1 equiv.), 4-methylpent-3-en-2-one (5.5 g, 1 equiv.) and DBU (7.1 g, 2 equiv.) in THF (60 mL). The crude product was purified by FC with hexane/MTBE 96:4 to yield 4-methyl-4-(phenethylthio)pentan-2-one as a colorless liquid (6.33 g, 74%).

Odor (1% wt/vol in EtOH on blotter after 24 h): bee's wax, fruity, cassis $^1$H-NMR (CDCl$_3$, 400 MHz): 7.31-7.36 (m, 2H), 7.22-7.28 (m, 3H), 2.79-2.92 (m, 4H), 2.71 (s, 2H), 2.19 (s, 3H), 1.46 (s, 6H).

$^{13}$C-NMR (CDCl$_3$, 101 MHz): 206.8 (s), 140.7 (s), 128.5 (2d), 128.5 (2d), 126.4 (d), 54.6 (t), 43.7 (s), 36.0 (t), 32.3 (q), 29.9 (t), 28.5 (2q).

MS (EI, 70 eV): 236 (4, M$^+$), 145 (18), 138 (16), 105 (31), 104 (47), 103 (12), 99 (30), 91 (65), 83 (11), 77 (14), 43 (100).

Example 6: 4-((1-(3,3-Dimethylcyclohexyl)ethyl) thio)-4-methylpentan-2-one

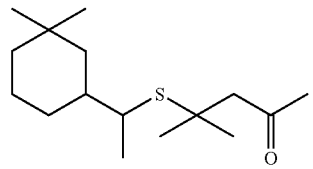 [SMILES: CC(=O)CC(C)(C)SC(C)C1CCCC(C)(C)C1]

6a) 1-(3,3-Dimethylcyclohexyl)ethane-1-thiol

This thiol was prepared according to the procedure described in example 3a) from 1-(3,3-dimethylcyclo-hexyl) ethanol and used without purification for the subsequent reaction described in Example 6b) below.

6b) 4-((1-(3,3-Dimethylcyclohexyl)ethyl)thio)-4-methylpentan-2-one

The procedure described in Example 1 was repeated with 1-(3,3-dimethylcyclohexyl)ethane-1-thiol (6.9 g, 40 mmol, 1 equiv.), 4-methylpent-3-en-2-one (7.86 g, 2 equiv.) and DBU (6.1 g, 1 equiv.) in THF (80 mL). The crude product was purified by FC with hexane/MTBE 96:4 to yield 4-((1-(3,3-dimethylcyclohexyl)ethyl)thio)-4-methylpentan-2-one as a colorless liquid (6.06 g, 56%, mixture of 2 diastereomers 96:4).

Odor (1% wt/vol in EtOH on blotter after 24 h): fruity, cassis, passionfruit $^1$H-NMR (CDCl$_3$, 400 MHz): (major diastereomer) 2.71 (s, 2H), 2.57-2.65 (m, 1H), 2.18 (s, 3H), 1.54-1.81 (m, 3H), 1.43 (2s, together 6H), 1.31-1.40 (m, 3H), 1.29 (d, J=7.1 Hz, 3H), 0.93-1.13 (m, 3H), 0.90 (d, J=12.2 Hz, 6H).

$^{13}$C-NMR (CDCl$_3$, 101 MHz): 206.9 (s), 55.4 (t), 44.3 (s), 43.2 (d), 42.4 (t), 40.2 (d), 39.2 (t), 33.5 (q), 32.4 (q), 30.8 (s), 29.8 (t), 28.9 (2q), 24.8 (q), 22.4 (t), 21.5 (q).

MS (EI, 70 eV): 270 (3, M$^+$), 171 (18), 138 (17), 123 (18), 99 (50), 95 (20), 83 (36), 69 (44), 55 (31), 43 (100), 41 (27).

Example 7: (Z)-4-Methyl-4-(non-6-en-1-ylthio)pentan-2-one

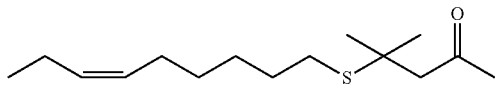 [SMILES: CC/C=C\CCCCCSC(C)(C)CC(C)=O]

7a) (Z)-Non-6-ene-1-thiol

This thiol was prepared according to the procedure described in example 3a) from (Z)-non-6-en-1-ol and used without purification for the subsequent reaction described in Example 7b) below.

7b) (Z)-4-Methyl-4-(non-6-en-1-ylthio)pentan-2-one

The procedure described in Example 1 was repeated with (Z)-non-6-ene-1-thiol (6.2 g, 39.2 mmol, 1 equiv.), 4-methylpent-3-en-2-one (7.69 g, 2 equiv.) and DBU (5.96 g, 1 equiv.) in THF (80 mL). The crude product was purified by FC with hexane/MTBE 96:4 to yield 4-((1-(3,3-dimethylcyclohexyl)ethyl) thio)-4-methylpentan-2-one as a colorless liquid (6.12 g, 61%).

Odor (1% wt/vol in EtOH on blotter after 24 h): green, fruity, cassis $^1$H-NMR (CDCl$_3$, 400 MHz): 5.25-5.45 (m, 2H), 2.69 (s, 2H), 2.54 (t, J=7.6 Hz, 2H), 2.20 (s, 3H), 1.97-2.10 (m, 4H), 1.52-1.64 (m, 2H), 1.42 (s, 6H), 1.34-1.45 (m, 4H), 0.96 (t, J=7.5 Hz, 3H).

$^{13}$C-NMR (CDCl$_3$, 101 MHz): 206.9 (s), 131.8 (d), 128.9 (d), 54.7 (t), 43.3 (s), 32.3 (q), 29.4 (t), 29.4 (t), 28.9 (t), 28.5 (2q), 28.1 (t), 26.9 (t), 20.5 (t), 14.4 (q).

MS (EI, 70 eV): 157 (31), 101 (16), 99 (22), 87 (20), 83 (17), 67 (16), 55 (27), 43 (100), 41 (30), 39 (15).

Example 8: (Z)-4-(Hex-3-en-1-ylthio)-4-methylpentan-2-one

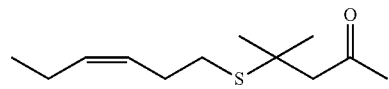

8a) (Z)-Hex-3-ene-1-thiol

This thiol was prepared according to the procedure described in example 3a) from (Z)-hex-3-en-1-ol and used without purification for the subsequent reaction described in Example 8b) below.

8b) (Z)-4-(Hex-3-en-1-ylthio)-4-methylpentan-2-one

The procedure described in Example 1 was repeated with (Z)-Hex-3-ene-1-thiol (2.8 g, 24.1 mmol, 1 equiv.), 4-methylpent-3-en-2-one (4.73 g, 2 equiv.) and DBU (3.67 g, 1 equiv.) in THF (60 mL). The crude product was purified by FC with hexane/MTBE 96:4 to yield (Z)-4-(hex-3-en-1-ylthio)-4-methylpentan-2-one as a slightly yellow liquid (2.23 g, 43%).

Odor (1% wt/vol in EtOH on blotter after 24 h): fresh green, fruity, cassis $^1$H-NMR (CDCl$_3$, 400 MHz): 5.31-5.50 (m, 2H), 2.70 (s, 2H), 2.55-2.59 (m, 2H), 2.26-2.34 (m, 2H), 2.19 (s, 3H), 2.00-2.10 (m, 2H), 1.43 (s, 6H), 0.97 (t, J=7.5 Hz, 3H).

$^{13}$C-NMR (CDCl$_3$, 101 MHz): 206.8 (s), 133.2 (d), 126.9 (d), 54.6 (t), 43.4 (s), 32.3 (q), 28.5 (2q), 28.2 (t), 27.2 (t), 20.6 (t), 14.2 (q).

MS (EI, 70 eV): 115 (48), 99 (31), 87 (10), 83 (8), 82 (9), 67 (11), 55 (14), 43 (100), 41 (22), 39 (12).

Example 9: 4-(Dodecylthio)-3-methylpentan-2-one

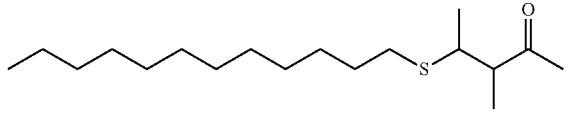 [SMILES: CCCCCCCCCCCCSC(C)C(C)C(C)=O]

The procedure described in Example 1 was repeated with 1-dodecanethiol (7.0 g, 34.6 mmol, 1 equiv.), (E)-3-methylpent-3-en-2-one (6.79 g, 2 equiv.) and DBU (5.27 g, 1 equiv.) in THF (60 mL). The crude product was purified by FC with hexane/MTBE 95:5 to yield 4-(dodecylthio)-3-methylpentan-2-one as a colorless liquid (9.4 g, 90%).

Odor (1% wt/vol in EtOH on blotter after 24 h): fruity, cassis $^1$H-NMR (CDCl$_3$, 400 MHz): (mixture of 2 diastereomers 48:52) 2.96-3.13 (m, 1H), 2.57-2.73 (m, 1H), 2.53 (t, J=7.5 Hz, 2H), 2.22 (s, 1.5H), 2.21 (s, 1.5H), 1.53-1.63 (m, 2H), 1.30 (d, J=6.8 Hz, 1.5H), 1.25-1.40 (m, 18H), 1.23 (d, J=7.0, 1.5H), 1.22 (d, J=7.0, 1.5H), 1.13 (d, J=6.8 Hz, 1.5H), 0.87-0.92 (m, 3H).

$^{13}$C-NMR (CDCl$_3$, 101 MHz): (mixture of 2 diastereomers 48:52) 211.1 (s), 210.7 (s), 52.5 (d), 51.9 (d), 42.6 (d), 41.1 (d), 31.9 (t), 31.4 (t), 31.0 (t), 29.8 (t), 29.7 (t), 29.7 (t), 29.6 (t), 29.6 (t), 29.5 (t), 29.3 (t), 29.2 (t), 29.0 (t), 22.7 (t), 20.5 (q), 18.0 (q), 14.4 (q), 14.1 (q), 12.8 (q).

MS (EI, 70 eV): 300 (5, M$^+$), 229 (20), 99 (40), 98 (24), 83 (29), 69 (25), 57 (19), 55 (51), 43 (100), 41 (40), 29 (24).

Example 10: 3-(Dodecylthio)-3-methylbutanal

The procedure described in Example 1 was repeated with 1-dodecanethiol (24.1 g, 119 mmol, 1 equiv.), 3-methylbut-2-enal (10.0 g, 1 equiv.) and DBU (18.1 g, 1 equiv.) without solvent. The crude product was purified by FC with hexane/MTBE 95:5 to yield 3-(dodecylthio)-3-methylbutanal as a colorless liquid (7.0 g, 21%).

Odor (1% wt/vol in EtOH on blotter after 24 h): cassis, sulfury $^1$H-NMR (CDCl$_3$, 400 MHz): 9.87 (t, J=2.9 Hz, 1H), 2.53-2.58 (m, 4H), 1.52-1.63 (m, 2H), 1.45 (s, 6H), 1.28-1.41 (m, 18H), 0.90 (t, J=6.8 Hz, 3H).

$^{13}$C-NMR (CDCl$_3$, 101 MHz): 202.0 (d), 54.6 (t), 42.7 (s), 32.3 (t), 30.0 (t), 30.0 (t), 30.0 (t), 29.9 (t), 29.8 (t), 29.7 (2q), 29.6 (2t), 29.6 (s), 28.4 (t), 23.1 (t), 14.5 (q).

MS (EI, 70 eV): 286 (2, M$^+$), 97 (35), 84 (50), 83 (54), 70 (32), 69 (47), 57 (89), 56 (73), 55 (100), 43 (53), 41 (77).

Example 11:
3-(Dodecylthio)-3-methylcyclohexan-1-one

The procedure described in Example 1 was repeated with 1-dodecanethiol (7.7 g, 38.0 mmol, 1 equiv.), 3-methyl-2-cyclohexen-1-one (5.03 g, 1.2 equiv.) and DBU (5.79 g, 1 equiv.) in THF (60 mL) during 4 days at room temperature. The crude product was purified by FC with hexane to hexane/MTBE 9:1 to yield 3-(dodecylthio)-3-methylcyclohexan-1-one as a colorless liquid (3.09 g, 26%).

Odor (1% wt/vol in EtOH on blotter after 24 h): aldehydic, floral, green, slightly sulfury $^1$H-NMR (CDCl$_3$, 400 MHz): 2.53-2.58 (m, 1H), 2.44-2.52 (m, 2H), 2.34-2.43 (m, 2H), 2.08-2.30 (m, 2H), 1.77-2.01 (m, 3H), 1.51-1.61 (m, 2H), 1.40 (s, 3H), 1.27-1.42 (m, 18H), 0.89 (t, J=6.8 Hz, 3H).

$^{13}$C-NMR (CDCl$_3$, 101 MHz): 208.9 (s), 53.5 (t), 48.3 (s), 40.3 (t), 36.8 (t), 31.9 (t), 29.6 (t), 29.6 (t), 29.6 (t), 29.5 (t), 29.4 (t), 29.3 (t), 29.2 (t), 29.2 (t), 28.8 (q), 27.4 (t), 22.7 (t), 22.1 (t), 14.1 (q).

MS (EI, 70 eV): 312 (1, M$^+$), 112 (21), 111 (100), 110 (36), 83 (30), 82 (56), 69 (29), 55 (78), 43 (32), 41 (42), 39 (22).

Example 12:
3-(Dodecylthio)-3-methylcyclopentan-1-one

The procedure described in Example 1 was repeated with 1-dodecanethiol (8.7 g, 43.0 mmol, 1 equiv.), 3-methylcyclopent-2-enone (4.96 g, 1.2 equiv.) and DBU (6.54 g, 1 equiv.) in THF (60 mL) during 4 days at room temperature. The crude product was purified by FC with hexane to hexane/MTBE 9:1 to yield 3-(dodecylthio)-3-methylcyclopentan-1-one as a colourless liquid (0.68 g, 5%).

Odor (1% wt/vol in EtOH on blotter after 24 h): fruity, sulfury $^1$H-NMR (CDCl$_3$, 400 MHz): 2.44-2.63 (m, 4H), 2.16-2.37 (m, 3H), 1.93-2.05 (m, 1H), 1.56 (s, 3H), 1.54-1.63 (m, 2H), 1.28-1.38 (m, 18H), 0.90 (t, J=6.6 Hz, 3H).

$^{13}$C-NMR (CDCl$_3$, 101 MHz): 216.9 (s), 52.7 (t), 49.1 (s), 36.9 (t), 36.1 (t), 31.9 (t), 29.6 (t), 29.6 (t), 29.6 (t), 29.5 (t), 29.3 (t), 29.2 (t), 29.2 (t), 28.8 (t), 28.3 (q), 22.7 (t), 14.1 (q).

MS (EI, 70 eV): 298 (4, M$^+$), 201 (19), 97 (100), 96 (41), 83 (19), 69 (52), 67 (19), 55 (35), 43 (32), 41 (48), 39 (18).

Example 13: 5-(Dodecylthio)-5-methylhexan-3-one

The procedure described in Example 1 was repeated with 1-dodecanethiol (4.9 g, 24.2 mmol, 1 equiv.), 5-methylhex-4-en-3-one (5.43 g, 2 equiv.) and DBU (3.69 g, 1 equiv.) in THF (80 mL) during 20 h at room temperature. The crude product was purified by FC with hexane/MTBE 96:4 to yield 5-(dodecylthio)-5-methylhexan-3-one as a colourless liquid (3.45 g, 46%).

Odor (1% wt/vol in EtOH on blotter after 24 h): fruity, sulfury, slightly aldehydic $^1$H-NMR (CDCl$_3$, 400 MHz): 2.68 (s, 2H), 2.54 (t, J=7.3 Hz, 2H), 2.50 (q, J=7.3 Hz, 2H), 1.52-1.62 (m, 2H), 1.43 (s, 6H), 1.27 (1.42-1.20, m, 18H), 1.05 (t, J=7.2 Hz, 3H), 0.89 (t, J=6.6 Hz, 3H).

$^{13}$C-NMR (CDCl$_3$, 101 MHz): 209.5 (s), 53.6 (t), 43.5 (s), 38.2 (t), 31.9 (t), 29.7 (t), 29.6 (t), 29.6 (t), 29.6 (t), 29.5 (t), 29.3 (t), 29.3 (2t), 28.6 (2q), 28.2 (t), 22.7 (t), 14.1 (q), 7.6 (q).

MS (EI, 70 eV): 314 (3, M$^+$), 257 (3), 243 (7), 201 (8), 113 (11), 97 (13), 83 (57), 69 (17), 57 (100), 43 (31), 29 (29).

Example 14: 4-(Decylthio)-4-methylpentan-2-one

The procedure described in Example 1 was repeated with 1-decanethiol (10.0 g, 57.4 mmol, 1 equiv.), 4-methylpent-3-en-2-one (11.26 g, 2 equiv.) and DBU (8.73 g, 1 equiv.) in THF (80 mL) during 24 h at room temperature. The crude product was purified by FC with hexane/MTBE 95:5 to yield 4-(decylthio)-4-methylpentan-2-one as a colourless liquid (14.12 g, 90%).

Odor (1% wt/vol in EtOH on blotter after 24 h): fruity, sulfury, slightly aldehydic.

$^1$H-NMR (CDCl$_3$, 400 MHz): 2.70 (s, 2H), 2.54 (t, J=7.8 Hz, 2H), 2.20 (s, 3H), 1.52-1.62 (m, 2H), 1.43 (s, 6H), 1.27 (1.43-1.23, m, 14H), 0.89 (t, J=6.6 Hz, 3H).

$^{13}$C-NMR (CDCl$_3$, 101 MHz): 206.9 (s), 54.7 (t), 43.3 (s), 32.4 (q), 31.9 (t), 29.5 (t), 29.5 (t), 29.3 (t), 29.3 (t), 29.3 (t), 28.5 (2q), 28.1 (t), 22.7 (t), 14.1 (q).

MS (EI, 70 eV): 272 (6, M+), 173 (17), 140 (4), 99 (26), 83 (24), 69 (9), 55 (23), 43 (100), 29 (11).

Example 15: 4-Methyl-4-(tetradecylthio)pentan-2-one

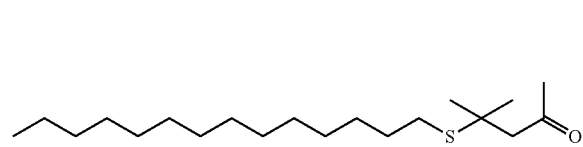 [SMILES: CCCCCCCCCCCCCCSC(C)(C)CC(C)=O]

The procedure described in Example 1 was repeated with 1-tetradecanethiol (4.16 g, 18.1 mmol, 1 equiv.), 4-methylpent-3-en-2-one (3.54 g, 2 equiv.) and DBU (2.75 g, 1 equiv.) in THF (50 mL) during 24 h at room temperature. The crude product was purified by FC with hexane/MTBE 95:5 to yield 4-methyl-4-(tetradecylthio)pentan-2-one as a colourless liquid (3.21 g, 54%).

Odor (1% wt/vol in EtOH on blotter after 24 h): fruity, sulfury, slightly aldehydic $^1$H-NMR (CDCl$_3$, 400 MHz): 2.70 (s, 2H), 2.54 (t, J=7.6 Hz, 2H), 2.21 (s, 3H), 1.53-1.62 (m, 2H), 1.43 (s, 6H), 1.25-1.42 (m, 22H), 0.89 (t, J=6.8 Hz, 3H).

$^{13}$C-NMR (CDCl$_3$, 101 MHz): 206.9 (s), 54.7 (t), 43.3 (s), 32.4 (q), 31.9 (t), 29.7 (t), 29.7 (t), 29.7 (2t), 29.6 (t), 29.5 (t), 29.5 (t), 29.4 (t), 29.3 (2t), 28.5 (2q), 28.1 (t), 22.7 (t), 14.1 (q).

MS (EI, 70 eV): 328 (3, M+), 285 (4), 271 (3), 229 (11), 168 (2), 111 (8), 99 (27), 83 (46), 69 (21), 55 (39), 43 (100), 29 (15).

Example 16: 4-Methyl-4-((6-methyloctyl)thio)pentan-2-one

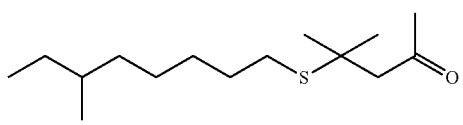 [SMILES: CCC(C)CCCCCSC(C)(C)CC(C)=O]

The procedure described in Example 1 was repeated with 6-methyloctane-1-thiol (prepared according to Example 3a) from 6-methyl octanol; 8.5 g, 53 mmol, 1 equiv.), 4-methylpent-3-en-2-one (10.4 g, 2 equiv.) and DBU (8.07 g, 1 equiv.) in THF (120 mL). The crude product was purified by FC with hexane/MTBE 96:4 to yield 4-methyl-4-((6-methyloctyl)thio)pentan-2-one as a clear, colorless liquid (9.3 g, 68%).

Odor (1% wt/vol in EtOH on blotter after 24 h): fruity, cassis, slightly aldehydic $^1$H-NMR (CDCl$_3$, 400 MHz): 2.69 (s, 2H), 2.59 (br. t, J=7.5 Hz, 2H), 2.19 (s, 3H), 1.52-1.63 (m, 2H), 1.42 (s, 6H), 1.22-1.41 (m, 7H), 1.06-1.19 (m, 2H), 0.85 (t, J=7.2 Hz, 3H), 0.84 (d, J=6.0 Hz, 3H).

$^{13}$C-NMR (CDCl$_3$, 101 MHz): 206.9 (s), 54.7 (t), 43.3 (s), 36.4 (t), 34.3 (d), 32.3 (q), 29.6 (t), 29.6 (t), 29.4 (t), 28.5 (2q), 28.1 (t), 26.7 (t), 19.2 (q), 11.4 (q).

MS (EI, 70 eV): 258 (3, M+), 159 (12), 99 (22), 97 (15), 83 (22), 69 (11), 57 (16), 55 (28), 43 (100), 41 (25), 29 (19).

Example 17: 3-((3-(4-Isobutyl-2-methylphenyl)propyl)thio)butanal

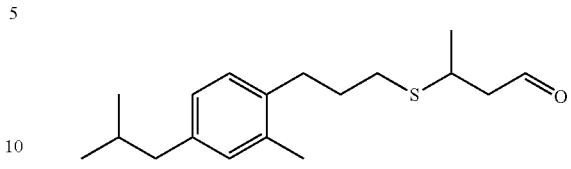

The procedure described in Example 3b) was repeated with 3-(4-isobutyl-2-methylphenyl)propane-1-thiol (prepared according to Example 3a) from 3-(4-isobutyl-2-methylphenyl)propan-1-ol {prepared as described in WO 2014/180945 A1}; 5.1 g, 22.9 mmol, 1 equiv.) and (E)-but-2-enal (3.21 g, 2 equiv.). The crude product was purified by FC with hexane/MTBE 94:6 to yield 3-((3-(4-isobutyl-2-methylphenyl) propyl)thio)butanal as a clear, colorless liquid (0.39 g, 6%).

Odor (1% wt/vol in EtOH on blotter after 24 h): aldehydic, sulfury $^1$H-NMR (CDCl$_3$, 400 MHz): 9.80 (t, J=2.0 Hz, 1H), 7.06 (d, J=7.6 Hz, 1H), 6.92-6.98 (m, 2H), 3.32 (sxt, J=6.8 Hz, 1H), 2.58-2.74 (m, 6H), 2.44 (d, J=7.1 Hz, 2H), 2.32 (s, 3H), 1.83-1.94 (m, 3H), 1.38 (d, J=6.6 Hz, 3H), 0.93 (d, J=6.6 Hz, 6H).

$^{13}$C-NMR (CDCl$_3$, 101 MHz): 200.6 (d), 139.4 (s), 136.7 (s), 135.4 (s), 131.1 (d), 128.6 (d), 126.7 (d), 50.5 (t), 45.0 (t), 34.1 (d), 32.0 (t), 30.4 (t), 30.2 (d), 30.1 (t), 21.7 (2q), 22.5 (q), 19.4 (q).

MS (EI, 70 eV): 292 (5, M+), 222 (35), 188 (17), 179 (47), 161 (36), 145 (100), 131 (43), 119 (41), 105 (19), 91 (15), 61 (9), 41 (24).

Example 18: 4-((3-(4-Isobutyl-2-methylphenyl)propyl)thio)-4-methylpentan-2-one

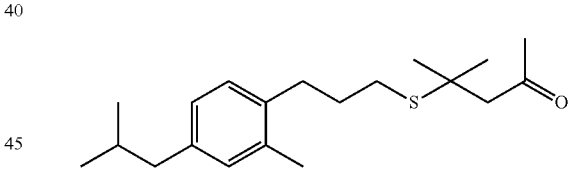

The procedure described in Example 1 was repeated with 3-(4-isobutyl-2-methylphenyl)propane-1-thiol (prepared according to Example 3a) from 3-(4-isobutyl-2-methylphenyl)propan-1-ol {prepared as described in WO 2014/180945 A1}; 5.1 g, 22.9 mmol, 1 equiv.), 4-methylpent-3-en-2-one (4.5 g, 2 equiv.) and DBU (3.49 g, 1 equiv.) in THF (50 mL). The crude product was purified by Kugelrohr distillation (140-165° C., 0.02 mbar) to yield 4-((3-(4-isobutyl-2-methylphenyl)propyl) thio)-4-methylpentan-2-one as a clear, colorless liquid (3.6 g, 49%).

Odor (1% wt/vol in EtOH on blotter after 24 h): fruity, cassis, sulfury $^1$H-NMR (CDCl$_3$, 400 MHz): 7.06 (d, J=7.6 Hz, 1H), 6.91-6.97 (m, 2H), 2.68-2.74 (m, 4H), 2.62 (t, J=7.3 Hz, 2H), 2.43 (d, J=7.3 Hz, 2H), 2.31 (s, 3H), 2.21 (s, 3H), 1.82-1.92 (m, 3H), 1.45 (s, 6H), 0.92 (d, J=6.6 Hz, 6H).

$^{13}$C-NMR (CDCl$_3$, 101 MHz): 206.9 (s), 139.4 (s), 136.8 (s), 135.4 (s), 131.1 (d), 128.6 (d), 126.6 (d), 54.7 (t), 45.0 (t), 43.5 (s), 32.3 (d), 32.3 (t), 30.2 (q), 30.1 (t), 28.5 (2q), 27.9 (t), 22.4 (2q), 19.3 (q).

MS (EI, 70 eV): 320 (6, M$^+$), 222 (27), 188 (44), 179 (37), 161 (50), 145 (100), 131 (60), 119 (43), 105 (20), 83 (24), 57 (14), 55 (23), 41 (79).

Example 19: Release of Odoriferous Volatiles from 4-(dodecylthio)-4-methylpentan-2-one A 10% wt/wt solution of 4-(dodecylthio)-4-methylpentan-2-one (prepared according to Example 1) in MTBE (200 µl, 16.3 mg) was applied on a paper blotter (4×1.2 cm$^2$, conditioned by rinsing with MeOH and vacuum drying). After 5 min evaporation of the solvent in open air, the blotter was placed at the bottom of a 2 L glass jar closed with a lid containing two openings which were sealed with Parafilm. The glass jar was left for 48 h at 25° C. in a cabinet lit with a fluorescent UV A/B-light source (ca. 0.8 mW/cm$^2$).

Then a stainless steel tube (length 25 cm, i.d. 0.8 mm) with a Porapak Q filter (cf. R. Kaiser, "Meaningful Scents around the World", Helvetica Chimica Acta, Zürich 2006, chapter 1.3.) attached to its tip with shrinking tube and secured with Parafilm, was introduced into the jar through one of the openings, to which it was attached by an air-tight Teflon joint. The tube was attached to a peristaltic pump with a thin rubber hose and the other opening of the jar (the air inlet) was equipped with a charcoal filter. An air volume of 2 L was drawn through the filter with a flow of 10 mL/min. The trapped volatiles were desorbed with 100 µL of MTBE and the liquid sample was analysed by GC/MS and GC-sniff. As shown in FIG. 1, the presence of the odorants 4-mercapto-4-methylpentan-2-one and dodecanal was detected among the volatiles released from 4-(dodecylthio)-4-methylpentan-2-one.

Figure 2:
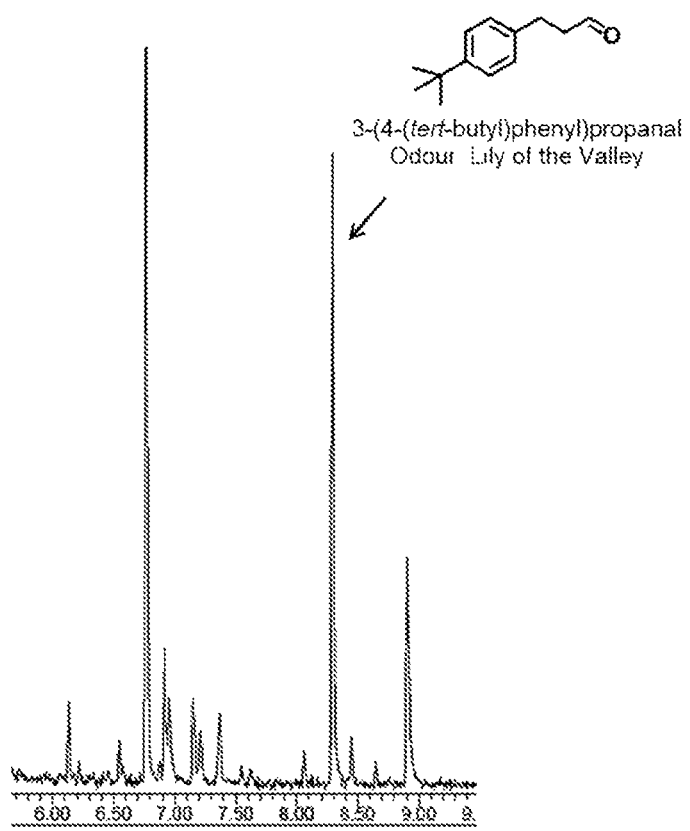

Example 20: Release of Odoriferous Volatiles from 3-((3-(4-(tert-butyl)phenyl)propyl) thio)butanal Example 19 was repeated with 3-((3-(4-(tert-butyl)phenyl)propyl)thio)butanal. The presence of the odorant 3-(4-(tert-butyl)phenyl)propanal was detected among the volatiles released from 3-((3-(4-(tert-butyl)phenyl)propyl)thio)butanal (FIG. 2).

Figure 3:
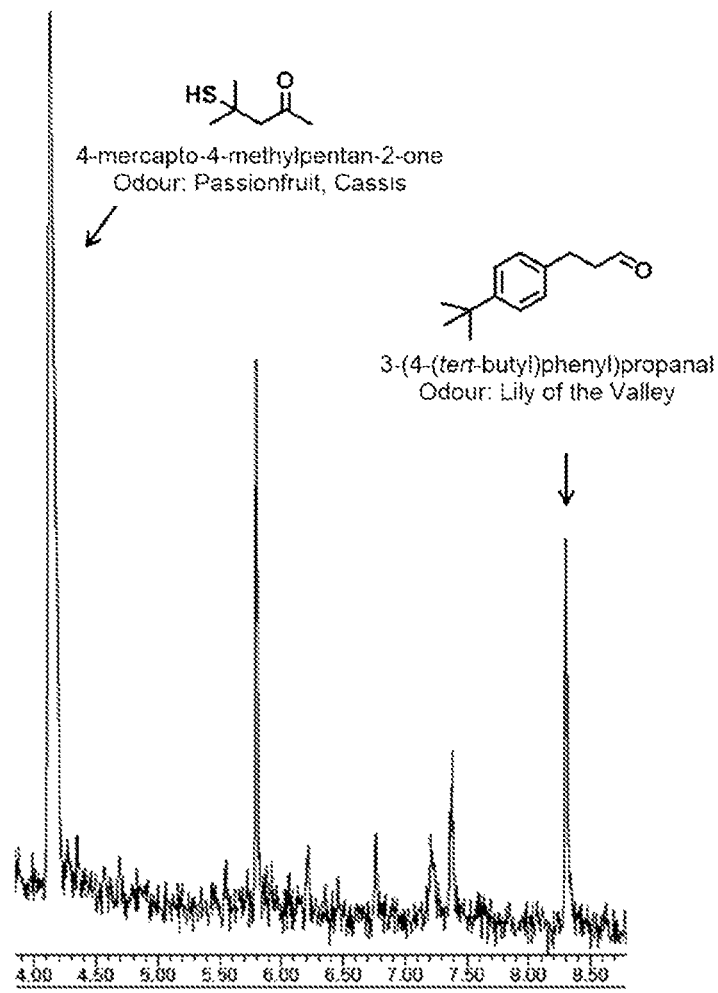

Example 21: Release of Odoriferous Volatiles from 4-((3-(4-(tert-butyl)phenyl)propyl) thio)-4-methylpentan-2-one Example 19 was repeated with 4-((3-(4-(tert-butyl)phenyl)propyl)thio)-4-methylpentan-2-one. The presence of the odorants 4-mercapto-4-methylpentan-2-one and 3-(4-(tert-butyl)phenyl)propanal was detected among the volatiles released from 4-((3-(4-(tert-butyl)phenyl)propyl)thio)-4-methylpentan-2-one (FIG. 3).

Example 22: A Fresh Clean Citrus Fragrance for an All-Purpose Cleaner

The following fragrance accord has been created for an all-purpose cleaner and is to be assessed at 0.3% in the unperfumed product base.

| CAS number | Ingredient name | Amount parts wt/wt |
|---|---|---|
| 140-11-4 | Benzyl acetate | 15 |
| 80-26-2 | Terpenyl Acetate | 60 |
| 101-86-0 | alpha Hexyl Cinnamic Aldehyde | 30 |
| 112-31-2 | Decanal | 18 |
| 67634-00-8 | Allyl amyl glycolate | 3 |
| 1092785-58-4 | Cassyrane ™ (Givaudan) | 0.5 |
| 106-22-9 | Citronellol | 20 |
| 68039-49-6 | Cyclal C | 5 |
| 57378-68-4 | delta Damascone | 1 |
| 65405-70-1 | 4-E-Decenal | 0.2 |
| 18479-58-8 | Dihydro Myrcenol | 60 |
| 8000-48-4 | *Eucalyptus* Essence | 10 |
| 67634-14-4 | Floralozone | 3 |
| 125109-85-5 | Florhydral | 2 |
| 14765-30-1 | Freskomenthe | 5 |
| 54464-57-2 | Iso E Super | 20 |
| 20665-85-4 | Isobutavan | 0.2 |
| 1335-46-2 | Isoraldeine 70 | 10 |
| 198404-98-7 | Javanol | 1 |
| 81783-01-9 | Labienoxime 1% in TEC/IPM | 3 |
| 61792-11-8 | Lemonile | 35 |
| 73018-51-6 | Lime Oxide | 20 |
| 78-70-6 | Linalool | 90 |
| 39255-32-8 | Manzanate | 2 |
| 37677-14-8 | Myraldene | 10 |
| 1637294-12-2 | Nympheal | 8 |
| 68647-72-3 | Orange Terpenes | 300 |
| 916887-53-1 | Petalia ™ (Givaudan) | 7 |
| 313973-37-4 | Pharaone ™ (Givaudan) 10% in DPG | 4 |
| 82461-14-1 | Rhubafuran | 0.5 |
| 1655500-83-6 | Rosyfolia ™ (Givaudan) | 3 |
| 16510-27-3 | Toscanol ™ (Givaudan) | 1 |

| | | Reference Accord | Accord A | Accord B |
|---|---|---|---|---|
| | 4-(dodecylthio)-4-methylpentan-2-one (Example 1) | 0 | 2 | 10 |
| 25265-71-8 | Dipropylene Glycol | 252.6 | 250.6 | 242.6 |
| | Total parts wt/wt | 1000 | 1000 | 1000 |

The olfactory character imparted to the product by the reference accord is citrus and fresh floral aldehydic, with a watery facette.

Addition of 0.2% of 4-(dodecylthio)-4-methylpentan-2-one (Example 1) enhances the citrus odor aspect, while addition of 1% renders the accord more intense citrus and enhances the juicy aspect. After 24 hours application on a floor tile, the perfume is slightly more intense with the addition of 0.2% 4-(dodecylthio)-4-methylpentan-2-one and clearly more intense, fresher and juicier than the reference with 1%.

Example 23: Olfacive Evaluation of Compound According to Example 1 and Mixtures Thereof with Mesityl Oxide Mixtures of the compound according to Example 1 (4-(dodecylthio)-4-methylpentan-2-one) with mesityl oxide were prepared in different ratios and subjected to olfactive evaluation. All samples were assessed as 10% solutions in ethanol on a fresh blotter.

| Sample | Olfacive evaluation |
|---|---|
| 4-(dodecylthio)-4-methylpentan-2-one | cassis, sulphur, *eucalyptus* bud, overall sulphurous impression is dominant, polarizing |

-continued

| Sample | Olfacive evaluation |
|---|---|
| 4-(dodecylthio)-4-methylpentan-2-one, spiked with 0.01 wt.-% or 0.03 wt.-% mesityl oxide | effect is minor, and olfactive profile still very close to pure material |
| 4-(dodecylthio)-4-methylpentan-2-one, spiked with 0.1 wt.-% mesityl oxide | combination starts to bring a positive olfactive benefit |
| 4-(dodecylthio)-4-methylpentan-2-one, spiked with 0.3 wt.-% mesityl oxide | combination brings a positive olfactive benefit, more juicy, more pleasant |
| 4-(dodecylthio)-4-methylpentan-2-one, containing 0.8% mesityl oxide | fruity juicy cassis, juicy, pleasant |
| 4-(dodecylthio)-4-methylpentan-2-one, spiked with 1.0 wt.-% mesityl oxide | combination brings a positive olfactive benefit, more juicy |
| 4-(dodecylthio)-4-methylpentan-2-one, spiked with 3.0 wt.-% mesityl oxide | mesityl oxide starts to dominate, and brings an additional green and technical facet |
| mesityl oxide | green, solvent, plastic like, then fruity, almondy, cherry |

The above results show that there is an optimum ratio between 4-(dodecylthio)-4-methylpentan-2-one and mesityl oxide, in which the mixture shows superior olfactive properties.

Example 24: Application in Liquid Detergent 1

Three samples of liquid detergent samples (34 g each) were prepared by adding 0.2 wt.-% of the following precursors according to the present invention to a non fragranced heavy duty liquid detergent base (pH 8.4): 4-(decylthio)-4-methylpentan-2-one (Example 14), 4-(dodecylthio)-4-methylpentan-2-one (Example 1) and 4-methyl-4-(tetradecylthio)pentan-2-one (Example 15). The samples were used to wash a load of 5 cotton terry towels (ca. 200 g dry weight each, 1.1 kg total load) in a standard front-loading washing machine. The wash cycle was carried out at 40° C., followed by two cold rinse cycles and spinning at 1000 rpm. The washed towels were assessed blind by a panel of 6 experienced evaluators for fragrance intensity on wet towel and after 24 h line dry at room temperature. The intensity was indicated on a scale from 0 (odorless) to 5 (very strong).

| Ingredient | Fragrance intensity on wet towel | Fragrance intensity on dry towel (24 h line dry) |
|---|---|---|
| 4-(decylthio)-4-methyl-pentan-2-one | 1.5 | 0.8 |
| 4-(dodecylthio)-4-methylpentan-2-one | 1.2 | 2.1 |
| 4-methyl-4-(tetradecylthio)pentan-2-one | 1.0 | 1.3 |

As can be seen from the results provided in the table above, the comparative study of three precursors according to the present invention with $R_1=R_3=R_4$=methyl, $R_2=R5$=H and $R_6$=nonyl, undecyl or tridecyl, the strongest precursor effect was observed with $R_6$=undecyl. The observed differencies between $R_6$=undecyl and $R_6$=nonyl or $R_6$=tridecyl were significant at confidence levels of 99.8% and 96%, respectively.

Due to the high volatility and water solubility of the released odorant 4-mercapto-4-methyl-2-pentanone (clogP=1.0, as compared to clogP=7.2 for 4-(dodecylthio)-4-methylpentan-2-one), it would not have been technically possible to deposit a sufficient amount of the material on fabric to trigger a fragrance impact.

Example 25: Application in Liquid Detergent 2 a) General

As series of experiments was conducted in order to determine whether fragrance ingredients according to the present invention show intensity benefits in fabric detergents. The compound of Example 1 (4-(dodecylthio)-4-methylpentan-2-one) was tested with two fragrances A and B, which had different olfactive profiles. The products were assessed on wet cloth and on 1 day, 3 days and 7 days dried cloth.

The members of a sensory analysis panel were selected on a basis of their olfactory sensory acuity and then trained for several months. Their training enabled them to identify individual odor characteristics and score their perceived intensity against given standards in a consistent manner.

The fabrics were washed in European washing machines (40° C.-1,000 spin/min) with one unit dose per wash load. For the wet stage, after washing, the cloths were placed into 500 mL wide necked glass jars ready for assessment. For the dry cloth assessment, the cloth was lined-dried and left overnight in a perfume free room at 25° C. Cloths washed with fragrance A were used as the control.

For all stages the overall perceived intensity was assessed by the trained sensory panel using a 0-100 linear scale. All overall perceived intensities were scaled against a reference sample A, for which the overall perceived intensity was set at 35 for wet cloth assessment and 10 for the dry cloth assessments where the reference sample was a 1 day dry cloth. The reference sample A was presented in the same format as the test samples for the wet cloth and dry cloth assessment.

For the wet cloth assessment, each sample was assessed twice by 20 panellists, thus giving 40 assessments per product. For the 1 day, 3 days and 7 days dry cloth assessments, each sample was assessed twice by 14 panellists, thus giving 28 assessments per product.

The estimated product means are reported on the next pages, together with any statistically significant differences between products.

b) Wet Cloth

| Product | Overall Perceived Intensity | Significance of Differences |
|---|---|---|
| Fragrance A | 35.7 | A |
| Fragrance A + 2% Precursor | 35.8 | A |
| Fragrance B | 44.6 | B |
| Fragrance B + 2% Precursor | 45.2 | B |

Where the same letter is shown in the "significance of differences" column there are no statistically significant differences between the relevant figures.

When assessed from wet cloth, cloth washed with Fragrance B or Fragrance B+2% precursor were not perceived to be significantly different, but were perceived to be significantly stronger than cloth washed with Fragrance A or Fragrance A+2% precursor, which were also not perceived to be significantly different to each other.

c) Dry Cloth 1 Day

| Product | Overall Perceived Intensity | Significance of Differences |
|---|---|---|
| Fragrance A | 10.9 | A |
| Fragrance A + 2% Precursor | 23.4 | B |
| Fragrance B | 12.3 | A |
| Fragrance B + 2% Precursor | 27.3 | C |

Where the same letter is shown in the "significance of differences" column there are no statistically significant differences between the relevant figures.

When assessed from 1 day dry cloth, cloth washed with Fragrance A+precursor was perceived to be significantly stronger than cloth washed with Fragrance A. Cloth washed with Fragrance B was perceived to be significantly weaker than cloth washed with Fragrance B+precursor.

d) Dry Cloth 3 Days

| Product | Overall Perceived Intensity | Significance of Differences |
|---|---|---|
| Fragrance A | 11.1 | A |
| Fragrance A + 2% Precursor | 22.9 | C |
| Fragrance B | 16.0 | B |
| Fragrance B + 2% Precursor | 26.1 | D |

Where the same letter is shown in the "significance of differences" column there are no statistically significant differences between the relevant figures.

When assessed from 3 day dry cloth, cloth washed with Fragrance B+2% precursor was perceived to be significantly stronger than cloth washed with any of the other products. Whereas, cloth washed with Fragrance A was perceived to be significantly weaker than cloth washed with any of the other products.

e) Dry Cloth 7 Days

| Product | Overall Perceived Intensity | Significance of Differences |
|---|---|---|
| Fragrance A | 14.1 | A |
| Fragrance A + 2% Precursor | 23.1 | B |
| Fragrance B | 15.6 | A |
| Fragrance B + 2% Precursor | 25.2 | B |

Where the same letter is shown in the "significance of differences" column there are no statistically significant differences between the relevant figures.

When assessed from 7 day dry cloth, cloth washed with Fragrance A+2% precursor or Fragrance B+2% precursor were not perceived to be significantly different, but were perceived to be significantly stronger than cloth washed Fragrance A or Fragrance B which were also not perceived to be significantly different to each other.

f) Conclusion

When assessed from wet cloth, for both Fragrance A and Fragrance B, the cloth washed with product containing the precursor was comparable in terms of strength to cloth washed with product not containing the precursor. When assessed from 1 day, 3 day and 7 day dry cloth, for both Fragrance A and Fragrance B, the cloth washed with product containing the precursor was perceived to be significantly stronger than the same fragrance without the precursor.

Example 26: Application in All-Purpose Cleaner a) General

As series of experiments was conducted in order to determine whether fragrance ingredients according to the present invention show intensity benefits in all purpose cleaners (APCs). The compound of Example 1 (4-(dodecyl-thio)-4-methylpentan-2-one) was tested with two fragrances A and B, which had different olfactive profiles. The products were assessed in booths on the floor at fresh (time=0) and after 1 hour, 2 hours and 4 hours application.

The members of a sensory analysis panel were selected on a basis of their olfactory sensory acuity and then trained for several months. Their training enabled them to identify individual odor characteristics and score their perceived intensity against given standards in a consistent manner.

The testing was carried out in small booths (10 $m^3$ booths, 21° C., 50% RH) specifically designed. The booths were closed during testing, with the doors sealed. The APC products were diluted at 1.2% in warm water (45° C.+/−2° C.). 60 mL of the diluted product was applied directly to the booth floor. It was evenly spread using a gloved hand, over an area of 65 cm×65 cm.

The system was assessed through a porthole in the door of the booth. The overall perceived intensity was assessed by the trained sensory panel using a 0-100 line scale. The dilution assessment was conducted over four sessions. The Fresh (time=0), 1 hour and 4 hour stages were assessed by 16 panelists, thus giving 32 assessments per product. The 2 hour stage was assessed by 17 panelists, thus giving 34 assessments per product.

The estimated product means are reported on the next pages, together with any statistically significant differences between products.

b) Fresh (time=0) bloom from floor assessment

| Product | Overall Perceived Intensity | Significance of Differences |
|---|---|---|
| Fragrance A | 33.8 | A |
| Fragrance A + 5% Precursor | 33.7 | A |
| Fragrance B | 36.5 | A |
| Fragrance B + 4% Precursor | 37.8 | A |
| Fragrance B + 8% Precursor | 36.5 | A |

Where the same letter is shown in the "significance of differences" column there are no statistically significant differences between the relevant figures.

When the products were assessed fresh (time=0), there was no perceived significant difference between the booths containing any of the five products tested.

c) One hour bloom from floor assessment

| Product | Overall Perceived Intensity | Significance of Differences |
|---|---|---|
| Fragrance A | 28.8 | A |
| Fragrance A + 5% Precursor | 37.9 | C |
| Fragrance B | 33.1 | B |
| Fragrance B + 4% Precursor | 35.4 | BC |
| Fragrance B + 8% Precursor | 37.0 | C |

Where the same letter is shown in the "significance of differences" column there are no statistically significant differences between the relevant figures.

When the products were assessed after 1 hour application, booths containing Fragrance B+8% precursor or Fragrance A+5% precursor were not perceived to be significantly different to booths containing Fragrance B+4% precursor, but were perceived to be significantly stronger than booths containing Fragrance A or Fragrance B.

d) Two Hour Bloom from Floor Assessment

| Product | Overall Perceived Intensity | Significance of Differences |
|---|---|---|
| Fragrance A | 21.6 | A |
| Fragrance A + 5% Precursor | 29.2 | B |
| Fragrance B | 18.2 | A |
| Fragrance B + 4% Precursor | 19.5 | A |
| Fragrance B + 8% Precursor | 31.1 | B |

Where the same letter is shown in the "significance of differences" column there are no statistically significant differences between the relevant figures.

When the products were assessed after 2 hours application, the booths containing Fragrance A+5% precursor or Fragrance B+8% precursor, which were not perceived to be significantly different, were perceived to be significantly stronger than the booths containing Fragrance A, Fragrance B or Fragrance B+4% precursor, which were also not perceived to be significantly different to each other.

e) Four Hour Bloom from Floor Assessment

| Product | Overall Perceived Intensity | Significance of Differences |
|---|---|---|
| Fragrance A | 20.4 | B |
| Fragrance A + 5% Precursor | 28.6 | C |
| Fragrance B | 10.8 | A |
| Fragrance B + 4% Precursor | 20.8 | B |
| Fragrance B + 8% Precursor | 27.2 | C |

Where the same letter is shown in the "significance of differences" column there are no statistically significant differences between the relevant figures.

When the products were assessed after 4 hours application, the booths containing Fragrance B+8% precursor or Fragrance A+5% precursor, which were not perceived to be significantly different, were perceived to be significantly stronger than booths containing Fragrance A or Fragrance B+4% precursor, which were also not perceived to be significantly different to each other. Furthermore, booths containing Fragrance B were perceived to be significantly weaker than the booths containing any of the other four products tested.

f) Conclusion

Fragrance A+5% precursor was comparable in terms of strength to Fragrance A at fresh (time=0), but was perceived to be significantly stronger than Fragrance A when assessed 1 hour, 2 hours and 4 hours after application.

The Fragrance B+8% precursor was comparable in terms of strength to Fragrance B at fresh (time=0) but was perceived to be significantly stronger than Fragrance B when assessed 1 hour, 2 hours and 4 hours after application. Whereas Fragrance B+4% precursor was comparable in terms of strength to Fragrance B at the fresh, 1 hour and 2 hour assessments, but was perceived to be significantly stronger than Fragrance B when assessed 4 hours after application.

Furthermore, Fragrance A+5% precursor and Fragrance B+8% precursor were comparable in terms of strength when assessed at all time points (0, 1, 2 and 4 hours).

The invention claimed is:

1. A method of generating a compound selected from the group consisting of a compound of formula (II) and a compound of formula (III) by decomposition of a compound of formula (I)

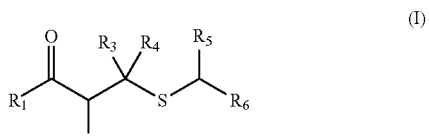

(I)

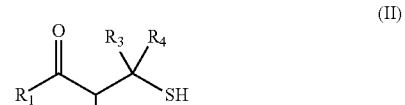

(II)

(III)

wherein $R_1$ is H or $C_{1-3}$ alkyl; $R_2$ is H or $C_{1-5}$-alkyl; $R_3$ is H or $C_{1-5}$-alkyl; and $R_4$ is $C_{1-6}$-alkyl; or $R_1$ and $R_4$ together with the carbon atoms to which they and $R_2$ are attached form a 5, 6 or 7 membered ring; $R_2$ is H or $C_{1-4}$-alkyl; and $R_3$ is H or $C_{1-4}$-alkyl; and wherein $R_5$ is H or a residue comprising 1 to 20 carbon atoms; and $R_6$ is a residue comprising 3 to 20 carbon atoms.

2. The method according to claim 1, wherein the total combined number of carbon atoms of $R_1$, $R_2$, $R_3$ and $R_4$ is 1 to 6.

3. The method according to claim 2, wherein $R_6$ is a residue comprising 7 to 16 carbon atoms.

4. The method according to claim 3, wherein $R_6$ is a residue comprising 8 to 14 carbon atoms.

5. The method according to claim 2, wherein $R_6$ is an alkyl, alkenyl or aromatic residue.

6. The method according to claim 2, wherein the compound of formula (I) is selected from the group consisting of 3-(octylthio)butanal, 4-methyl-4-(octylthio)pentan-2-one, 3-(decylthio)butanal, 4-(decylthio)-4-methylpentan-2-one, 4-(dodecylthio)pentan-2-one, 4-(dodecylthio)-4-methylpentan-2-one, 4-(dodecylthio)-3-methylpentan-2-one, 3-(dodecylthio)-3-methylbutanal, 3-(dodecylthio)butanal, 3-(dodecylthio)-3-methylcyclohexan-1-one, 3-(dodecylthio)-3-methylcyclopentan-1-one, 3-(tetradecylthio)butanal and 4-methyl-4-(tetradecylthio)pentan-2-one, 4-methyl-4-((6-methyloctyl)thio) pentan-2-one, 3-((3-(4-isobutyl-2-methylphenyl)propyl)thio)butanal and 4-((3-(4-isobutyl-2-methylphenyl)propyl)thio)-4-methylpentan-2-one.

7. The method according to claim 2, wherein the total combined number of carbon atoms of $R_1$, $R_2$, $R_3$ and $R_4$ is 1 to 5.

8. The method according to claim 7, wherein the total combined number of carbon atoms of $R_1$, $R_2$, $R_3$ and $R_4$ is 1 to 4.

9. The method according to claim 8, wherein the total combined number of carbon atoms of $R_1$, $R_2$, $R_3$ and $R_4$ is 1 to 3.

10. The method according to claim 1, wherein $R_1$ is H; $R_2$ is H; $R_3$ is H; and $R_4$ is methyl.

11. The method according to claim 1, wherein $R_1$ is H; $R_2$ is H; $R_3$ is methyl; and $R_4$ is methyl.

12. The method according to claim 1, wherein $R_1$ is methyl; $R_2$ is H; $R_3$ is H; and $R_4$ is methyl.

13. The method according to claim 1, wherein $R_1$ is methyl; $R_2$ is H; $R_3$ is methyl; and $R_4$ is methyl.

14. The method according to claim 1, wherein the decomposition of the compound of formula (I) comprises cleavage of the bond between the sulfur atom and the carbon atom in the δ-position to the carbonyl group which results in the compound selected from the group consisting of a compound of formula (II) and a compound of formula (III).

15. The method according to claim 1, wherein the compound of formula (II) which exhibits fragrance notes with a fruity, blackcurrant or passionfruit character.

16. A composition of matter comprising a compound of formula (I) and a compound of formula (A)

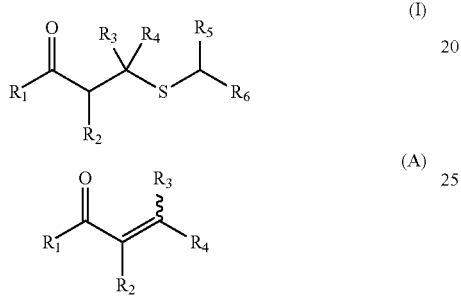

wherein $R_1$ is H or $C_{1-3}$alkyl; $R_2$ is H or $C_{1-5}$-alkyl; $R_3$ is H or $C_{1-5}$-alkyl; and $R_4$ is $C_{1-6}$-alkyl; or
$R_1$ and $R_4$ together with the carbon atoms to which they and $R_2$ are attached form a 5, 6 or 7 membered ring;
$R_2$ is H or $C_{1-4}$-alkyl;
$R_3$ is H or $C_{1-4}$-alkyl;
$R_5$ is H or a residue comprising 1 to 20 carbon atoms;
$R_6$ is a residue comprising 3 to 20 carbon atoms,
wherein the amount of the compound of formula (A) in relation to the total amount of the compound of formula (I) and the compound of formula (A) is 0.1 to 3.0 wt.-%.

17. A consumer product comprising a composition of matter according to claim 16.

18. The composition of matter according to claim 16, wherein the amount of the compound of formula (A) in relation to the total amount of the compound of formula (I) and the compound of formula (A) is 0.3 to 1.2 wt.-%.

19. The composition of matter according to claim 18, wherein the amount of the compound of formula (A) in relation to the total amount of the compound of formula (I) and the compound of formula (A) is 0.6 to 1.0 wt.-%.

20. The composition of matter according to claim 16, wherein the composition exhibits lesser thiol off-odors as compared to a like composition wherein the compound of formula (A) is excluded.

21. A consumer product comprising a compound of formula (I)

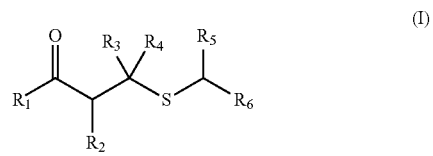

wherein $R_1$ is H or $C_{1-3}$ alkyl; $R_2$ is H or $C_{1-4}$-alkyl; $R_3$ is H or $C_{1-4}$-alkyl; and $R_4$ is $C_{1-4}$-alkyl; or
$R_1$ and $R_4$ together with the carbon atoms to which they and $R_2$ are attached form a 5, 6 or 7 membered ring;
$R_2$ is H or $C_{1-4}$-alkyl;
$R_3$ is H or $C_{1-4}$-alkyl;
$R_5$ is H or a residue comprising 1 to 20 carbon atoms;
$R_6$ is a residue comprising 6 to 20 carbon atoms; and wherein
the total combined number of carbon atoms of $R_1$, $R_2$, $R_3$ and $R_4$ is 1 to 4, preferably 1 to 3.

22. A consumer product according to claim 21, wherein the concentration of the compound of formula (I) is 0.1% to 10%.

23. The consumer product according to claim 21, wherein the total combined number of carbon atoms of $R_1$, $R_2$, $R_3$ and $R_4$ is 1 to 3.

* * * * *